(12) United States Patent
Burns et al.

(10) Patent No.: US 8,084,001 B2
(45) Date of Patent: Dec. 27, 2011

(54) PHOTOLUMINESCENT SILICA-BASED SENSORS AND METHODS OF USE

(75) Inventors: Andrew A. Burns, Ithaca, NY (US);
Erik Herz, Ithaca, NY (US); Tara C. Zedayko, Ithaca, NY (US); Ulrich Wiesner, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1139 days.

(21) Appl. No.: 11/119,969

(22) Filed: May 2, 2005

(65) Prior Publication Data

US 2006/0245971 A1 Nov. 2, 2006

(51) Int. Cl.
*G01N 33/00* (2006.01)

(52) U.S. Cl. ............... 422/402; 422/82.08

(58) Field of Classification Search ............ 422/58, 422/68.08, 402, 82.08
See application file for complete search history.

(56) References Cited

U.S. PATENT DOCUMENTS

| | | | |
|---|---|---|---|
| 4,275,300 A * | 6/1981 | Abbott | 250/304 |
| 4,279,617 A | 7/1981 | Masson et al. | |
| 4,774,339 A | 9/1988 | Haugland et al. | |
| 4,810,636 A | 3/1989 | Corey | |
| 4,812,409 A | 3/1989 | Babb et al. | |
| 4,957,487 A | 9/1990 | Gerow | |
| 5,026,377 A | 6/1991 | Burton et al. | |
| 5,187,288 A | 2/1993 | Kang et al. | |
| 5,248,782 A | 9/1993 | Haugland et al. | |
| 5,260,957 A | 11/1993 | Hakimi et al. | |
| 5,274,113 A | 12/1993 | Kang et al. | |
| 5,433,896 A | 7/1995 | Kang et al. | |
| 5,498,549 A * | 3/1996 | Nagel et al. | 436/172 |
| 5,639,603 A | 6/1997 | Dower et al. | |
| 5,830,912 A | 11/1998 | Gee et al. | |
| 5,981,180 A | 11/1999 | Chandler et al. | |
| 5,990,479 A | 11/1999 | Weiss et al. | |
| 6,180,415 B1 | 1/2001 | Schultz et al. | |
| 6,207,392 B1 | 3/2001 | Weiss et al. | |
| 6,251,303 B1 | 6/2001 | Bawendi et al. | |
| 6,268,222 B1 | 7/2001 | Chandler et al. | |
| 6,274,323 B1 | 8/2001 | Bruchez et al. | |
| 6,306,610 B1 | 10/2001 | Bawendi et al. | |
| 6,319,426 B1 | 11/2001 | Bawendi et al. | |
| 6,322,901 B1 | 11/2001 | Bawendi et al. | |

(Continued)

FOREIGN PATENT DOCUMENTS

WO WO9610282 4/1996

(Continued)

OTHER PUBLICATIONS

OW, Hooisweng, et al. "Fluorescent Silica Nanoparticles for Single Particle Tracking Experiments of Rat Mast Cells", National Conference: MRS Symposium, Boston, MA (Nov. 27, 2001).

(Continued)

*Primary Examiner* — Sam P Siefke
(74) *Attorney, Agent, or Firm* — Harris Beach PLLC

(57) ABSTRACT

Sensor particles comprise a silica-based core and at least one photoluminescent dye. The silica-based core may comprise a plurality of pores and the at least one photoluminescent dye may comprise a reference dye, insensitive to its environment and analytes and a sensor dye, sensitive to either or both of the foregoing. The sensor particles may be employed to sense unknown environmental conditions or analytes in biological or non-biological systems, in vitro or in vivo.

16 Claims, 4 Drawing Sheets

U.S. PATENT DOCUMENTS

| | | | |
|---|---|---|---|
| 6,326,144 | B1 | 12/2001 | Bawendi et al. |
| 6,344,272 | B1 | 2/2002 | Oldenburg et al. |
| 6,423,551 | B1 | 7/2002 | Weiss et al. |
| 6,426,513 | B1 | 7/2002 | Bawendi et al. |
| 6,428,811 | B1 | 8/2002 | West et al. |
| 6,444,143 | B2 | 9/2002 | Bawendi et al. |
| 6,454,789 | B1 | 9/2002 | Chen et al. |
| 6,479,146 | B1 | 11/2002 | Caruso et al. |
| 6,500,622 | B2 | 12/2002 | Bruchez, Jr. et al. |
| 6,548,264 | B1 | 4/2003 | Tan et al. |
| 6,576,219 | B2 | 6/2003 | Brandt et al. |
| 6,649,138 | B2 | 11/2003 | Adams et al. |
| 6,805,702 | B1 | 10/2004 | Chen et al. |
| 2003/0017264 | A1 | 1/2003 | Treadway et al. |
| 2004/0101822 | A1 | 5/2004 | Wiesner et al. |
| 2005/0216047 | A1 | 9/2005 | Kumoyama et al. |
| 2006/0178721 | A1 | 8/2006 | Durcan et al. |
| 2006/0293695 | A1 | 12/2006 | Ricci et al. |
| 2008/0033570 | A1 | 2/2008 | Blitz et al. |

FOREIGN PATENT DOCUMENTS

| | | |
|---|---|---|
| WO | WO9950916 | 10/1999 |
| WO | WO-03/095648 A1 | 11/2003 |

OTHER PUBLICATIONS

OW, Hooisweng et al., "Project Abstract", Poster Session: NYSTAR CAT: Biotechnology, (Apr. 23, 2000).

OW, Hooisweng et al., "Silica Based Fluorescent CU-Dots for Single Particle Tracking Experiments", Poster Session: Nanobiotechnology Center (NBTC), (Jun. 25, 2002).

OW, Hooisweng, et al., "Synthesis and Characterization of Functional Silica Nanoparticles for Labeling, Tracking and Filler Applications", Poster session: Cornell Polymer Outreach Program, (May 20, 2002).

Srivastava, Mamta et al., "Single Particle Tracking of Fluor-escent Silica Nanoparticles Bound to lgE Receptors on RBL Mast Cells", *National Conference: Biophysical Soc. Symposium*, San Francisco (Spring 2002).

Stober, Werner et al., "Controlled Growth of Monodisperse Silica Spheres in the Micron Size Range", Journal of Colloid and Interface Science, vol. 26, (1968), 62-69.

Dabbousi BQ: "(CDSE)ZNS Core-Shell Quantum Dots: Synthesis and Characterizations of a Size Series of Highly Luminescent Nano-Crystallites" Journal of Physical Chemistry B, Materials, Surfaces Interfaces and Biophysical (Nov. 13, 1997) vol. 101, No. 46.

Kuno M: The band edge luminescence of surface modified CDSE Nanocrystallites: probing the luminescence physics, vol. 106, No. 23, (Jun. 15, 1997).

Bruchez et al., Science, Sep. 25, 1998, 281 (5385), pp. 2013-2016.

Lal. et al., Chem. Mater., Sep. 2000, 12(9), pp. 2632-2639.

A Real-Time Ratiometric Method for the Determination of Molecular Oxygen Inside Living Cells Using Sol-Gel-Based Spherical Optical Nanosensors w/Applications to Rat C6 Glioma, Department of Chemistry and Department of Environmental Health Sciences, University of Michigan, Ann Arbor MI 48109-1055, Aug. 3, 2001.

Synthesis and Characterization of Colloidal Dispersions of Fluorescent, Monodisperse Silica Spheres, A. Van Blaaderen and A. Vrij, pp. 2921-2931.

Three-Dimensional Imaging of Submicrometer Colloidal Particles in Concentrated Suspensions Using Confocal Scanning Laser Microscopy, A. Van Blaaderen, A. Imhof, W. Hage and A. Vrij, pp. 1514-1517.

Real-Time Measurements of Dissolved Oxygen Inside Live Cells by Organically Modified Silicate Fluorescent Nanosensors, Dept. of Chemistry and Dept. of Environmental Health Sciences, U of MI, Ann Harbor, MI 48109, and Dept. of Chemical Engineering, Apr. 2, 2004.

Communications, Dye Loading of Amphiphilic Poly(organosiloxane) Nanoparticles, (2003) (pp. 1713-1717).

Dye-labeled Pol(organosiloxane) Microgels with Core-Shell Architecture, Christina Graf et al., (pp. 6170-6180).

International Searching Authority, PCT/ISA/220, Notification of Transmittal of the International Search Report and the Written Opinion of the International Searching Authority, or the Declaration, dated Jul. 1, 2009, 1 pg.

Patent Corporation Treaty, PCT/ISA/210, International Search Report, dated Jul. 1, 2009, 2 pgs.

European Patent Office, Supplementary European Search Report, dated Mar. 27, 2009, 10 pgs.

Patent Corporation Treaty, PCT/IB/373, International Preliminary Report on Patentability, dated Nov. 6, 2007, 1 pg.

International Search Authority, PCT/ISA/237, Written Opinion of the International Searching Authority dated Aug. 24, 2007, 5 pgs.

Talanta, Elsevier, Buck, Sarah M, et al., Nanoscale probes encapsulated by biologically localized embedding (PEBBLEs) for icon sensing and imaging in live cells, vol. 63 (2004) 41-59, 19 pgs.

J. American Chemical Society 1998, 120, 11092-11095, Tapan Kumar Jain, et al., Nanometer Silica Particles Encapsulating Active Compounds: A Novel Ceramic Drug Carrier, 1998, 4 pgs.

Current Opinion in Chemical Biology, Elsevier, Sarah M. Buck, et al., Optochemical nanosensor PEBBLEs: photonic explorers for bioanalysis with biologically localized embedding, 2004, 8:540-546, 7 pgs.

Nano Letters, American Chemical Society, Lin Wang, et al., Dual-Luminophore-Doped Silica Nanoparticles for Multiplexed Signaling, vol. 5, No. 1, 2005, 37-43, 8 pgs.

Koo, Yong-Eun Lee et al., "Real-Time Measurements of Dissolved Oxygen Inside Live Cells by Organically Modified Silicate Fluorescent Nanosensors", May 1, 2004 Analytical Chemistry, vol. 76, No. 9 (pp. 2498-2505).

Jungmann, Nadja et al., "Dye Loading of Amphiphilic Poly(organosiloxane) Nanoparticles", Apr. 17, 2003 Angew. Chem. Int. Ed., vol. 42, Issue 15 (pp. 1714-1717).

\* cited by examiner

PHOTOLUMINESCENT SILICA-BASED SENSORS AND METHODS OF USE

STATEMENT OF GOVERNMENT RIGHTS

This invention was made with Government support under contract number DMR-0079992, awarded by the National Science Foundation Materials Research Science and Engineering Center. The government has certain rights in this invention.

FIELD OF INVENTION

The present invention relates to silica-based particles and more particularly to silica-based particles comprising photoluminescent species adapted for use as sensing agents.

BACKGROUND

The technology behind photoluminescent imaging has evolved substantially in recent years, towards high resolution, real time, molecular-level analysis to visualize and understand life and its processes. The appeal of photoluminescence-based assays stems from their excellent contrast, high specificity and fast response times.

Although the majority of photoluminescent dyes are designed to be insensitive to their surroundings, a variety of dyes have been synthesized with specific affinity and response to chemical analytes or environmental stimuli. Certain types of photoluminescent dyes, for example, have been used free in solution as sensors responsive to chemical analytes or environmental stimuli.

Although both sensing and insensitive photoluminescent compounds are often used free in solution, in some cases, these dyes have been integrated into sensing platforms such as optical fibers, thin films and membranes. The composition of the sensing platform as well as the identity of the photoluminescent dye may impact the properties of the dye in addition to determining the types of unknown conditions subject to investigation its sensing capabilities.

There is a need for an environmental or analyte sensor that can optimize the variable properties of photoluminescent dyes and sense unknown conditions in a variety of environments.

SUMMARY OF INVENTION

The present invention concerns improved sensor particles for detecting a variety of environmental conditions and analytes. The present invention also concerns methods of using these particles in sensing applications.

Briefly, the sensor particles of the present invention comprise a core and at least one photoluminescent dye.

In certain embodiments, the core is a silica-based nanoparticle and the at least one photoluminescent dye includes a reference dye and a sensor, at least one of which may be covalently bonded to the core. The reference dye may be positioned within the core and the sensor dye may be positioned on at least a portion of a surface of the core. Alternatively, the reference dye and the sensor dye may be positioned on or over the core. Further, the silica-based particle may comprise a silica-based shell surrounding the core, wherein the reference dye is positioned within the core and the silica-based shell is interposed between the reference dye and the sensor dye. In other embodiments, one of the reference and sensor dyes comprises between about 1.0 and about 1000.0 dye molecules per sensor particle and the reference and sensor dyes emit photons in response to a single or multiple wavelength excitation source. The wavelengths of peak emission of the reference and sensor dyes in response to appropriate excitation are typically separated by a sufficient gap to individually discern their emission peaks.

In still other embodiments, the core comprises a plurality of pores, at least one of which includes a diameter between about 0.1 nm and about 100.0 nm and more particularly between about 2.0 nm and about 50.0 nm. The diameter of the silica-based particle may be between about 1.0 nm. and about 250.0 nm.

Methods of the present invention comprise use of the sensor particles to sense unknown environmental conditions or analytes.

In one embodiment, the method comprises the steps of providing at least one silica-based particle comprising two or more photoluminescent dyes, introducing the at least one silica-based particle into an environment comprising an unknown condition or analyte, exposing the at least one silica-based particle to excitation photons, such that each of the two or more photoluminescent dyes emits photons, recording the photons emitted by the two or more photoluminescent dyes, and determining the unknown environmental condition or analyte from these data. This method may further comprise excitation of the two or more photoluminescent dyes with photons in the presence of a known environmental condition or analyte and comparing resulting emission waves of the two or more photoluminescent dyes in the presence of the known environmental condition or analyte. Under these circumstances, the emission taken in the presence of the known environmental condition or analyte may be used to generate comparison data, which is correlated to the known condition or analyte. Thus, the determining step may include using the comparison data to determine the unknown condition or analyte. The determining step may also comprise simultaneous interrogation of multiple sensor dyes whose emission peaks may be deconvolved to yield the status of multiple unknown conditions or analytes.

In another embodiment, a method of determining an unknown condition in an organism comprises the steps of providing a silica-based nanoparticle comprising a sensor dye that emits photons, inserting the silica-based nanoparticle into the organism exciting the sensor dye with photons, detecting the photoluminescent emission of the sensor dye, and determining the unknown condition of the organism. The sensor dye may emit photons at infrared or near infrared wavelengths. The silica-based nanoparticle may be positioned within a cell, tissue, blood or other bodily fluids of the organism.

BRIEF DESCRIPTION OF THE DRAWINGS

Certain embodiments of the presently claimed invention are illustrated by the accompanying figures. It should be understood that the figures are not necessarily to scale and that details that are not necessary for an understanding of the invention or which render other details difficult to perceive may be omitted. It should be understood, of course, that the invention is not necessarily limited to the particular embodiments illustrated herein.

DETAILED DESCRIPTION

Figure 1A:
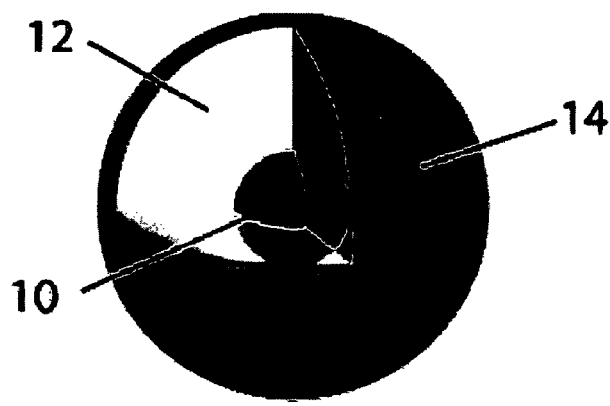
FIG. 1A is a perspective view of one embodiment of the silica-based particles of the present invention in partial cross-section.

The silica-based particles of the present invention are typically nanoparticles and comprise a silica-based core and two or more photoluminescent dyes. As used herein, the term core means a central or foundational part. Silica used for forming the silica-based matrix may include the general formula $R_{4-n}SiX_n$, where X can be a hydrolyzable group, such as ethoxy, methoxy or 2-methoxy-ethoxy, R can be an organic group (for example methyl or ethyl) and n is an integer from 1 to 4. The two or more photoluminescent dyes comprise a reference dye and a sensor dye. As used herein, the term reference dye means a dye that is substantially insensitive to its environment and/or any analytes present therein or exhibits the same or substantially the same photon emissions upon exposure to excitation photons in different environments. The term sensor dye means any dye that is sensitive or responsive to its environment and/or analytes or exhibits different photon emissions upon exposure to photons in different environments or analytes. In certain embodiments, the reference and sensor dyes may be covalently bound to the silica-based matrix. In other embodiments, the dyes may be incorporated into the silica-based matrix through physical entrapment without covalent linkages or adsorbed onto the surface of the matrix.

In one embodiment, associating the reference and sensor dyes with a silica-based matrix can enhance brightness of the dyes and discourage photobleaching (i.e. the dyes stay brighter longer). In these embodiments, silica-based particles of the present invention may exhibit enhanced brightness levels as compared to the free dye in solution, as measured, for example, by photoluminescent correlation spectroscopy.

In another embodiment, the silica-based matrix comprises pores or interstices, which allow fluids or analytes to penetrate the silica-based matrix and interact directly with the sensor dye positioned therein. In this way, sensing capability may be enhanced. The pores typically include diameters between about 0.1 nanometers and about 100.0 nanometers. Pore size may display a heterogeneous distribution, ranging in size from 2.0 nanometers to about 50 nanometers and up.

In another embodiment, use of a silica-based matrix enables excitation of two or more dyes with a single excitation wavelength. For reference and sensor dyes which exhibit discernable emission peaks, varying the number of molecules of each dye per particle may allow dye combinations that normally require multiple excitation wavelengths to respond to a single excitation wavelength. For instance, if the reference dye requires a longer excitation wavelength than the sensor dye for emission, additional reference dye molecules may be associated with the silica-based matrix to increase its relative absorption, so that both dyes respond measurably to the same excitation wavelength. The silica-based matrix can incorporate between about 1.0 and about 1000.0 dye molecules per particle, with between 2.0 and 100.0 dye molecules being typical.

In yet another embodiment, the silica-based matrix may include more than one sensor dye for sensing more than one environmental condition or analyte. Assuming that the emission wavelengths of the incorporated dyes are far enough apart to discern separate emission peaks, between about one and about seven and more particularly between about two and five distinct sensor dyes may be associated with the silica-based matrix for separate sensing applications.

Silica-based particles of the present invention may also incorporate additives. A core of superparagmagnetic material, such as nano-sized iron oxide or other magnetic alloys or oxides and/or one or more of a multitude of functional groups may be positioned on particle surfaces for various purposes. For example, the particles can be conjugated with antibodies or therapeutic agents to identify and treat disease states or conditions. The therapeutic agent can be absorbed into the pores of the silica-based matrix or coated on a surface of the particles.

The surface of the final silica-based particles can be functionalized with a wide variety of surface modifiers, including amines, antibodies, microorganisms, viruses, enzymes, receptors, haptens, hormones, or combinations thereof. The use of amine groups, such as aminopropyl and methylaminopropyl groups, creates positive surface charges which are attracted to the negative charge of a cell surface. The use of alkyl groups, such as methyl or dodecyl chains, creates a non-charged surface, allowing the particles to exist in hydrophobic environments—within a cell membrane for example. Further, functional silica-conjugated groups are available to react with a variety of species, including polymers for example: polyethylene glycol (PEG), cross-linkers and other surface modifiers, such as carboxylic acids, esters or biotin, which may be used to attach other moeties to the particle surface, including peptides, DNA, antibodies and avidin/streptavadin. The surface modifier can comprise a layer surrounding the particle, which is selectively permeable to certain analytes. The layer is interposed between the sensor dye and the environment.

Functionalizing the surface of the particles with the appropriate surface modifier may also allow use of the particles in a multitude of target environments. For example, the addition of a hydrophobic coating allows the particles to be dispersed in a hydrophobic environment. Along these lines, selection of the appropriate surface modifier can lead to preferential interaction, defined as a relative increase in the likelihood of a particular desired interaction. Examples include functionalization of particle surfaces with at least one antibody having an affinity for antigens on cell surfaces and/or use of a coating comprising biotin and avadin/streptavadin, which preferentially interacts with biotin in target environments.

As previously mentioned, the two or more photoluminescent dyes may comprise a reference dye and a sensor dye. The peak emission wavelengths of the reference and sensor dyes are typically separated by a sufficient wavelength gap to individually discern their peaks upon excitation at the same wavelength.

The reference dye is typically sequestered within the silica-based particle, usually in its core. Although the reference dye is substantially insensitive to its environment and analytes, sequestering the reference dye within the particle serves as a precautionary measure to avoid interaction with the target environment or analyte, to the extent some sensitivity does exist. Suitable reference dyes include, but are not limited to, the following:

| Reference Dye Name | $\lambda_{ex}/\lambda_{em}$(nm) | Integration Method | Emission |
|---|---|---|---|
| Molecular Probes AlexaFluor 350 | 350/445 | NHS Ester | Near UV |
| Molecular Probes Pacific Blue | 416/451 | NHS Ester | Visible |
| Molecular Probes AlexaFluor 488 | 488/520 | NHS Ester | Visible |
| Molecular Probes AlexaFluor 532 | 530/555 | NHS Ester | Visible |
| Rhodamine B Isothiocyanate | 540/573 | Isothiocyanate | Visible |
| Tetramethylrhodamine Isothiocyanate | 550/580 | Isothiocyanate | Visible |
| Molecular Probes AlexaFluor 568 | 580/602 | NHS Ester | Visible |
| Dyomics DY 610 | 609/629 | NHS Ester | Visible |
| Dyomics DY 615 | 621/641 | NHS Ester | Visible |
| Molecular Probes AlexaFluor 647 | 651/672 | NHS Ester | Visible |
| Dyomics DY 675 | 674/699 | NHS Ester | Near IR |
| Dyomics DY 700 | 702/723 | NHS Ester | Near IR |
| Dyomics DY 731 | 736/759 | NHS Ester | Near IR |
| Dyomics DY 776 | 771/801 | NHS Ester | Near IR |
| Sigma Aldrich NIR 797 | 795/835 | Isothiocyanate | Near IR |
| Dyomics DY 485 XL | 488/560 | NHS Ester | MegaStokes™ |
| Dyomics DY 510 XL | 488/630 | NHS Ester | MegaStokes™ |

So-called MegaStokes™ dyes are defined here as dyes that exhibit differences between their excitation and emission wavelengths between about 30.0 nm to about 200.0 nm.

The sensor dye is typically placed at or near a surface of the silica-based particle to increase its interaction with the environment and/or any analytes. Under this construction, the sensor dye is more likely to come into direct contact with the environmental condition or analyte undergoing investigation. Emissions of sensor dyes are subject to environmental or analyte stimuli. Depending on pH of the environment, pH sensor dyes, for example, exhibit varying emission spectra based on changes in the sensor dye's electronic state, through the addition or subtraction of protons. The presence of metal ions may cause diminished emissions by quenching the sensor dye.

The following table is a non-exhaustive list of a number of suitable sensor dyes as well as their environmental or analyte sensitivities.

| Sensor Dye Name | $\lambda_{ex}/\lambda_{em}$(nm) | Sensitivity | Integration Method | Emission |
|---|---|---|---|---|
| Fluorescein Isothiocyanate | 485/500 | pH (pKa = 6.4) | Amine Conjugation | Visible |
| β-5-carboxyfluorescein-bis-(5-carboxymethoxy-2-nitrobenzyl) ether-alanine-carboxamide, succinimidyl ester | 490/520 | Caged Fluorophore + pH | Amine Conjugation | Visible |
| Fluo-4 Iodoacetamide | 494/516 | $Ca^{+2}$ | Thiol Conjugation | Visible |
| 5-carboxy-2',7'-dichlorosulfonefluorescein | 500/530 | pH (pKa = 6.4) | Amine Conjugation | Visible |
| Carboxy Seminaphthofluorescein (SNAFL-1) NHS ester | 510-575/545-636 | Spectral Shift pH (pKa = 7.7) | Amine Conjugation | Visible |
| Oregon Green 514 Carboxylic Acid, NHS ester | 511/530 | pH (pKa = 4.6) | Amine Conjugation | Visible |
| Erythrosin B Isothiocyanate | 530/555 | Oxygen | Amine Conjugation | Visible |
| Sigma Aldrich NIR667-NHS | 667/685 | Amino Acids | Amine Conjugation | Near IR |
| Fluorescein | 485/500 | pH (pKa = 6.4) | Dextran-bound | Visible |
| Fluo-4 | 488/530 | $Ca^{+2}$ | Dextran-bound | Visible |
| Calcium Green | 488/535 | $Ca^{+2}$ | Dextran-bound | Visible |
| 2',7'-bis-(2-carboxyethyl)-(5/6)-carboxyfluorescein | 488/535 | pH (pKa = 7.0) | Dextran-bound | Visible |
| Seminapthorhodafluor-1 (SNARF-1) | 514/560-640 | Spectral Shift pH (pKa = 7.5) | Dextran-bound | Near IR |
| 4',5'-dichloro-2',7'-dimethoxyfluorescein | 520/550 | pH (pKa = 6.4) | Dextran-bound | Visible |
| X-Rhod | 575/620 | $Ca^{+2}$ | Dextran-bound | Visible |
| PBFI (spectral Shift) | 338/557-507 | $K^+$ | Physical Entrapment | Mega Stokes |
| 6-methoxy-N-(3-sulfopropyl)quinolinium | 344/443 | $Cl^-$ | Physical Entrapment | Near UV |
| Zinquin Ethyl Ester | 364/385 | $Zn^{+2}$ | Physical Entrapment | Near UV |
| Diaminonapthalene | 370/440 | Nitric Oxide | Physical Entrapment | Visible |
| Calcium Yellow | 435/550 | $Ca^{+2}$ | Physical Entrapment | Visible |
| 4,5-Diaminofluorescein | 488/530 | Nitric Oxide | Physical Entrapment | Visible |
| 4-amino-5-methylamino-2',7'- difluorofluorescein | 488/525 | Nitric Oxide | Physical Entrapment | Visible |
| Calcium Green | 490/540 | $Ca^{+2}$ | Physical Entrapment | Visible |
| Magnesium Green | 490/540 | $Mg^{+2}$ | Physical Entrapment | Visible |
| Dihydrorhodamine | 500/536 | Nitric Oxide | Physical Entrapment | Visible |
| Calcium Orange | 540/580 | $Ca^{+2}$ | Physical Entrapment | Visible |
| CoroNa Red | 547/576 | $Na^+$ | Physical Entrapment | Visible |
| RhodZin-3 | 550/575 | $Zn^{+2}$ | Physical Entrapment | Visible |
| Resorufin ethers (benzyl, ethyl, methyl, etc.) | 560/580 | Enzyme Activity + pH Lifetime | Physical Entrapment | Visible |

-continued

| Sensor Dye Name | $\lambda_{ex}/\lambda_{em}$(nm) | Sensitivity | Integration Method | Emission |
|---|---|---|---|---|
| Sulforhodamineamidoethyl mercaptan | 561/581 | Selenium | Physical Entrapment | Visible |
| Boron dipyrromethane (BODIPY 665-676) | 665/676 | Reactive Oxygen | Physical Entrapment | Near IR |

So-called caged dyes may be employed as the sensor dye. Caged dyes are a class of photoluminescent dyes whose photoluminescent state is activated by their environment. In other words, caged dyes enter their working environment in a non-photoluminescent state and are turned "on" by external events that modify the chemical structure of the dye. Caged dyes typically comprise a covalent attachment of particular groups to a main conjugated ring structure. Activation may occur when the covalent attachment is cleaved due to environmental stimuli. For example, resorufin (7-hydroxy-3H-phnoxazin-3-one) is the parent dye of a family of caged dyes that utilize a cleavable ether attachment.

Figure 1B:
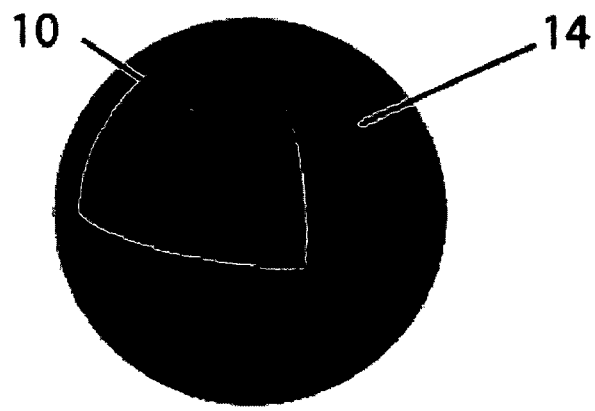
FIG. 1B is a perspective view of another embodiment of the silica-based particles of the present invention in partial cross-section.
Figure 1C:
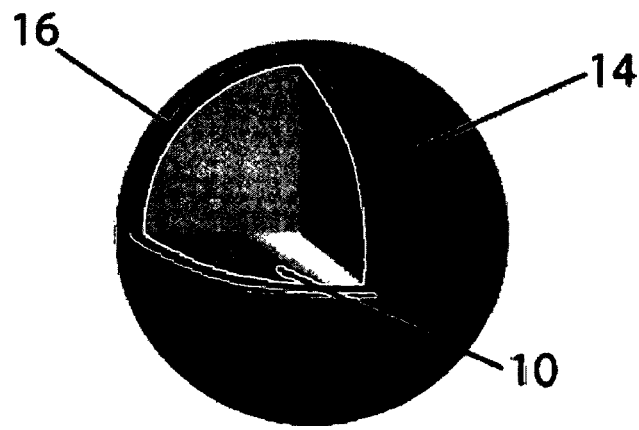
FIG. 1C is a perspective view of yet another embodiment of the silica-based particles of the present invention in partial cross-section.
Figure 1D:
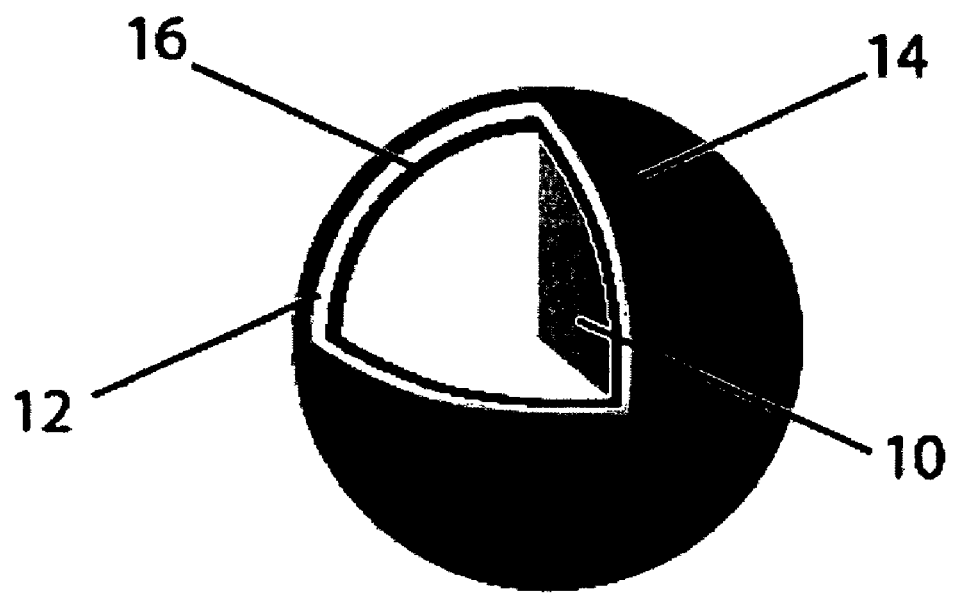
FIG. 1D is a perspective view of yet another embodiment of the silica-based particles of the present invention in partial cross-section.

The dyes may be incorporated into a silica-based matrix in various configurations. Referring now to FIGS. 1A, 1B, 1C and 1D, different architectures for the silica-based particles of the present invention are shown. As seen in FIG. 1A, the silica-based particles include an internal core 10 comprising a silica-based matrix and the reference dye, an intermediate silica-based shell 12, and an external shell 14 comprising the sensor dye. In this embodiment, the intermediate silica-based shell is interposed between the reference and sensor dyes. The intermediate silica-based shell may solely comprise a silica-based material without the presence of photoluminescent dye or in the presence of minimal photoluminescent dye (e.g., less than 5% by weight). As seen in FIG. 1B, the silica-based particles include an internal core, 10, comprising a silica-based matrix and the reference dye and an external shell 14 comprising the sensor dye. As seen in FIG. 1C, the silica-based particles comprise an internal core 10 comprising a silica-based matrix, a first shell 16 comprising the reference dye and a second shell 14 surrounding the first shell and comprising the sensor dye. As seen in FIG. 1D, the silica-based particles include an internal core 10, comprising a silica-based matrix, a first shell 16 comprising the reference dye, an intermediate shell 12 surrounding the first shell and comprising another silica-based matrix and an outer shell 14 surrounding the inner shells and comprising the sensor dye. In these embodiments, the diameter of the core may be between about 2.0 nanometers and tens of microns and typically between about 25.0 nanometers and 200.0 nanometers. The thickness of the first and subsequent shells may be between about 1.0 nanometer to about 400.0 nanometers and typically between about 10.0 nanometers to about 50.0 nanometers. The first and subsequent shells may cover from about 10.0 percent to about 100.0 percent of the surface area of the particles. Thus, the size of the particles may be between about 10.0 nm and tens of microns, and more particularly between about 10.0 nm and about 1.0 micron.

There are a number of ways to synthesize the silica-based particles of the present invention. The particles may, for example, be created using the sol-gel process. Sol-gel chemistry allows the synthesis of silica-based particles under benign conditions, such as room temperature and without the use of harmful chemicals. Alternatively, reverse micelles may be employed as reactors for particle synthesis. Reverse micelles are stable suspensions of a polar aqueous phase within a hydrophobic solvent, mediated by amphiphilic surfactant molecules.

The Stöber sol-gel process typically yields silica-based particles that include covalent linkages to the reference and sensor dyes. In general, silica-based particles of the present invention can be prepared through the Stöber sol-gel process by mixing a reactive reference dye with a co-reactive organosilane compound to form a reactive photoluminescent organosilane compound that can be co-condensed to form a core, followed by conjugation of a sensor dye to the core by mixing the core particle with the sensor dye and additional co-reactive organo/alkoxysilanes.

The sol-gel process may, however, be modified depending on the desired architecture of the particles. As previously mentioned, the silica-based particles of the present invention may exhibit various configurations, including an internal core comprising a silica-based matrix and a reference dye and an external shell comprising a sensor dye (FIGS. 1A and 1B) and an internal core comprising a silica-based matrix, a first shell comprising the reference dye and an outer shell surrounding the first shell and comprising the sensor dye (FIGS. 1C and 1D).

Preparation of the silica-based particles of FIG. 1A comprises synthesis of the core, subsequent growth of a silica intermediate shell and formation of the sensor dye-rich silica shell. Synthesis of the core typically occurs in three steps. First, in an inert gas atmosphere, a silane compound is coupled to the reference dye at a mole ratio of silane to reference dye of about 50:1 in degassed ethanol to form a photoluminescent silane compound. This product—the reference dye conjugate—is then added under ambient conditions to an absolute ethanolic solution of ammonia and water, under vigorous stirring. A silica precursor, such as tetraethoxysilane, is then promptly added to yield a final reaction solution of reference dye conjugate, silica precursor, ammonia and water in concentrations of $1.7 \times 10^{-5}$ M, 0.05 M, 0.2 M and 0.855 M. This reaction proceeds for 12-18 hrs and produces dye-rich silicate cores, with diameters of about 5.0 nanometers. To this solution, additional silica precursor is slowly added to grow a silica shell, in an amount of about $5.55 \times 10^{-6}$ M per minute, to reach a final reaction condition of reference dye conjugate, silica precursor, ammonia and water of $1.7 \times 10^{-5}$ M, 1.055 M, 0.5 M and 0.855 M.

Figure 2A:
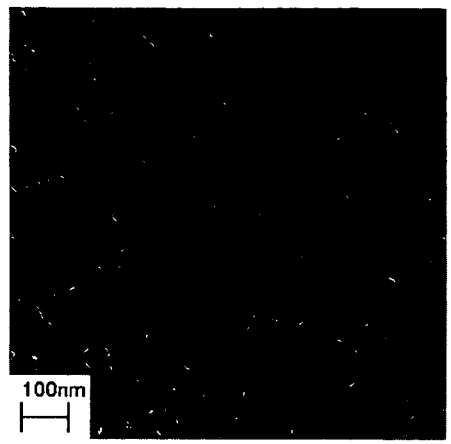
FIG. 2A is a scanning electron microscope image of the silica-based particles of FIG. 1A.

To prepare the core/shell particles for conjugation with the sensor dye, the particles are dialyzed once against ethanol for approximately 24 hours. The dialyzed solution is then diluted to avoid agglomeration of the particles during the sensor dye coupling reaction. The sensor dye is conjugated to the silane in a similar manner as above for the reference dye to form sensor dye conjugate, though in this case the molar ratio is much lower (i.e., 2:1 molar ratio of silane to sensor dye), to avoid excess amination of the particles during functionalization. This serves the dual purposes of avoiding agglomeration of particles and helping to prevent amines on the surface from inhibiting the sensor dye's ability to sense. Thereafter, the sensor dye conjugate is mixed with a silica precursor in ethanol at a molar ratio of sensor dye conjugate to silica precursor of about $1.2 \times 10^{-5}$ M to 0.0125 M. This mixture is added drop-wise to the dialyzed solution of core/shell particles. After the solution is allowed to react, it is dialyzed against absolute ethanol, where it remains stable for at least several months without agglomeration. The final particles, shown in a scanning electron microscope at FIG. 2A are approximately 40.0 nanometers in diameter.

Figure 2B:
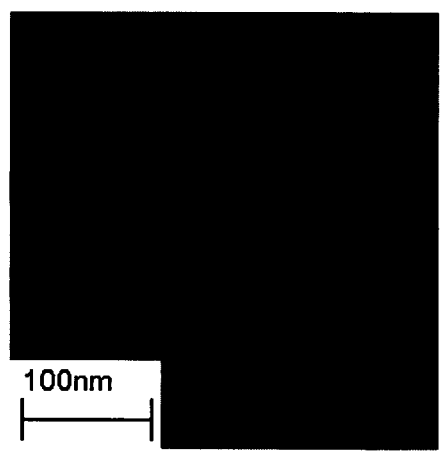
FIG. 2B is scanning electron microscope image of the silica-based particles of FIG. 1B.

The size of the core as well as the size of the particles made with the sol-gel process can be altered. The synthesis that leads to the particle architecture shown in FIG. 1B follows. Silica and a reference dye conjugate, per above, are co-condensed in an ethalonic solution at concentrations of $2.13 \times 10^{-5}$ M reference dye conjugate, 0.2 M silica precursor, 0.625 M ammonia and 1.45 M water to yield monodisperse core particles of about 55.0 nanometers in diameter. To this mixture, sensor dye conjugate and additional silica precursor are added drop wise to yield a final reaction condition of $2.13 \times 10^{-5}$ M reference dye conjugate, $2.13 \times 10^{-5}$ M sensor dye conjugate, 0.254M silica precursor, 0.625 M ammonia and 1.45 M water. These particles, which lack an intermediate silica shell between the core and the sensor dye-containing outer shell, are then centrifuged and re-suspended twice in ethanol and twice in water to remove excess reagents. As shown in FIG. 2B, the final particles are approximately 60.0 to 80.0 nanometers in size and comprise a relatively large reference dye-rich core and a sensor dye-rich shell.

Figure 2C:
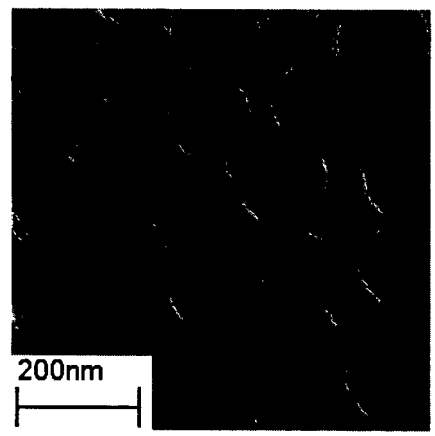
FIG. 2C is scanning electron microscope image of the silica-based particles of FIG. 1C.

Preparation of the silica particle architecture shown in FIG. 1C entails slight modifications to foregoing processes. Silica precursor, ammonia and water at ratios of 0.17 M to 1.0M to 2.5M are combined in absolute ethanol under ambient conditions, with vigorous stirring. After the solution reacts, the reaction product is collected by centrifugation and re-suspended by ultrasonication with water and ethanol. The seed particles, comprised of silica, are then re-suspended in absolute ethanol with water and ammonia, followed by drop-wise addition of a pre-combined solution of silica precursor, reference conjugate and ethanol to yield a final reaction condition of reference conjugate, silica precursor, ammonia and water of 1.16M, 0.027M, 0.2M, and 2.0M, respectively. Following reaction for 12-18 hours, the particles are centrifuged and washed repeatedly with absolute ethanol and deionized water. A similar synthesis was preformed to create a sensor dye shell on these particles, using a sensor dye conjugate synthesized in ethanol under inert atmosphere and a 50.0 to 1.0 molar ratio of organosilane to sensor dye. The final particles, shown at FIG. 2C, are approximately 200.0 nanometers in size and comprise a silica-rich core surrounded by a first reference dye rich shell surrounded by a second sensor dye rich shell. In the fourth particle architecture, FIG. 1D, an intermediate silica shell, between the reference and sensing dye layers is introduced by condensing pure silica precursors onto the first shell to ensure further protection of the encapsulated reference dye.

To prepare the silica-based particles of the present invention using reverse micelles to incorporate dyes which lack appropriate conjugation chemistries, a microemulsion synthesis protocol is followed. Silica-based seed particles, with reference dye, are first synthesized using the Stöber sol-gel process. These seed particles are transferred from ethanol into an aqueous environment via dialysis or centrifugation and washing. The reactive concentrations required for sufficient surface coating are calculated based on the number of available surface silanol groups which is dependent upon particle size as well as concentration. The particles and any dextran-bound or otherwise hydrophilic dyes are added in aqueous solution into a reverse microemulsion formed in cyclohexane in the presence of a charged or uncharged amphiphilic surfactant with or without co-surfactants, as needed. A concentrated solution of ammonia is added to catalyze condensation of a silica precursor, which is added last. One suitable surfactant/co-surfactant combination is Triton X-100® and n-hexanol.

A coating of about 2.0 to about 10.0 nanometers in thickness may be effectively attached to the particle surface in the presence of free dye molecules or dextran-bound dyes, which become trapped in the silica matrix as it forms, thus encapsulating the sensor dye molecules and creating a particle based sensor. In other words, rather than being covalently bonded to the silica-based matrix, the photoluminescent dyes are typically physically entrapped or entrained in the silica-based matrix. By adjusting the reaction pH and silica precursor concentrations, it is possible to tailor the porosity of the silica matrix to allow analytes to interface with entrapped dye molecules.

After the silica-based particles of the present invention have been synthesized, they may be used for sensing in both biological and non-biological systems. A number of sensing methodologies, including ratiometric sensing, spectral shift sensing and lifetime sensing are possible.

Environmental conditions as well as the presence and concentration of certain analytes, may be explored in biological and non-biological systems. The silica-based particles may be introduced into cells, cell membranes, tissues, prokaryotic systems (e.g., *E. coli* biofilms), solutions, reactions and bodies of water, like rivers and lakes. Several methods exist for introducing the silica-based particles into cells, including commercially available lipid vesicle based methods, microinjection, and antibody-specific uptake (during which a cell surface receptor mediates endocytosis of the particle). In phagocytic cells and some endocytic cells, uptake may occur spontaneously. Based on the brightness levels exhibited by the particles, measurements may advantageously be taken through incorporation of only a single silica-based particle of the present invention into the target environment. Multiple silica-based particles may, however, be employed.

Through the introduction of multiple classes of analyte-specific sensors to an unknown environment, multiplexed measurements may be achieved. Multiplexing allows simultaneous interrogation of multiple photoluminescent species whose emission peaks may be deconvolved to yield the status of multiple analytes. This approach would be well suited to high-throughput analysis of the effects of stimuli (such as novel therapeutics) on cellular function.

The silica-based particles may also be employed as sensors in various organisms, on animal cells or bodily fluids, including human cells or bodily fluids, such as blood or serum. Cells or fluids may be harvested and tested outside the body or a whole body imager may excite the dyes within the body and measure emission. In vitro sensing typically relies upon sensors comprising photoluminescent dyes in the visible spectrum. With in vivo testing, the sensors may be locally injected into a particular area or functionalized with antibodies that exhibit preferential interactions with certain cell surface receptors. Sensor dyes used for in vivo testing typically exhibit infrared or near infrared emission wavelengths.

The environmental conditions or analytes undergoing sensing may also vary. Environmental conditions, like pH levels and hydrophobic or hydrophilic states may be determined. The presence and concentration of ions, such as potassium, phosphate, sodium, calcium, copper, magnesium, chromium, chloride, fluoride and iron, heavy metals, such as cadmium, zinc, lead, selenium, mercury, nickel, as well as biomolecular substances, such as vitamins and amino acids, may also be evaluated.

Further, in vitro and in vivo testing with the silica-based particles of the present invention may advantageously be employed for ascertaining the redox status of cells within the body of a living organism. The redox status of a cell describes its oxidation-reduction potential (i.e., the potential of the cell to lose electrons (oxidation) versus its potential to gain electrons (reduction)). The energy on which cells rely is derived mainly from energy released through oxidation from organic molecules to oxygen, yielding an overall reducing environment within cells, which is carefully regulated. Externally or internally opposed challenges to the normal oxidative/reductive balance—redox stresses—have been shown to be indicative of negative cellular events, specifically tumorigenesis, and may be important in disease or injury states such as cancer and strokes.

The foregoing unknown conditions or analytes may be investigated through various sensing methodologies.

Ratiometric sensing, as used herein, means the determination of unknown environmental conditions based on ratios established for and corresponding to known environmental conditions. Major emission peak intensities of two or more photoluminescent dyes are measured under known environmental or analyte conditions. A calibration is performed by calculating ratios of peak emission for the two dyes (sensor dye/reference dye); the ratios correspond to known conditions. The calibration forms a basis for determinations of unknown conditions through excitation and emission intensity measurement of particles comprising the same reference and sensor dyes under the unknown condition.

Spectral-shift based measurements operate under similar principles. Unknown environmental or analyte conditions are investigated through the use of calibration curves that are established based on the wavelengths of maximal emission exhibited by reference and sensor dyes upon excitation under known conditions. Rather than relying upon ratios of peak emission intensities, however, the difference between maximum peak wavelengths ($\lambda_{max}$) for the reference and sensor dyes is used as the dependent variable.

Lifetime-based sensing measures the excited state lifetimes of two or more photoluminescent dyes, one of which whose lifetime is known to be environmentally insensitive, and at least one of which whose lifetime is dependent upon a specific environmental condition or analyte. The fluorescence lifetime ($\tau$) is the length of time that a photoluminescent dye spends in an excited state, from initial absorption of a photon until its emission; it is most often in the range from 10 ps to several nanoseconds. A calibration may be performed by measurement of the fluorescence lifetimes for multiple analyte concentrations, creating a basis for further concentration determinations.

To establish a baseline for the sensing, one or more particles are first introduced into an environment having known conditions. The particles are then excited by one or more selected wavelengths of a multi-photon light source, typically exhibiting an excitation wavelength between about 250.0 nm and about 800.0 nm, as appropriate for the absorption profiles of the reference and sensor dyes in the particle. Multiphoton excitation utilizes lasers (often Ti-Sapphire), which can be tuned to a variety of emission wavelengths. The long wavelength (700.0 nm to >1500.0 nm) photons are not readily absorbed by tissue or media but may induce multiphoton excitation in dye molecules at very high photon flux (i.e., at the focal point of the beam). While the reference dye typically exhibits a relatively constant wavelength and intensity of emission, the sensor dye exhibits emissions that correspond to environmental stimuli or to the presence or concentration of certain analytes.

Thus, after excitation of each of the reference and sensor dyes at specific levels, photon emissions may be measured. Measurement may be carried out using spectrofluorometry or fluorescence microscopy. Photoluminescent lifetime is measured using a pulsed laser source and a gated detector which measures the emission as a function of time following irradiation. Photoluminescent emission is collected in quartz or plastic cuvettes as a function of emission wavelength at 90 degrees to the excitation beam via photon counting on a photomultiplier tube or avalanche photodiode. With photoluminescent microscopy, images of individual cell-free samples comprising sensors subjected to different known conditions are collected. After photon emissions for the reference and sensor dyes are measured, emission ratios ($\gamma = I_{sensor}/I_{reference}$), spectral shifts or photoluminescent lifetimes are plotted versus the known environmental condition to establish calibration curves. That is, the emissions taken in the presence of the known environmental condition or analyte are used to generate comparison data, which is correlated to the known condition. For example, calibration curves indicate the range of ratios that correspond to the known environmental conditions (e.g., in one embodiment, ratios between about 0.5 and about 0.8 could correspond to a pH between 6 and 7).

After the comparison data have been generated, they may be used to ascertain unknown environmental conditions or the presence and concentration of analytes. Particle emissions are recorded in the presence of the unknown condition or analyte, and the data are used to determine the unknown condition by comparing it with the comparison data established for the known conditions.

The silica-based particles of the present invention can be used in a variety of other applications, such as those disclosed in co-owned co-pending U.S. application Ser. No. 10/306, 614, entitled "Fluorescent Silica Based Nanoparticles." All uses disclosed therein are hereby incorporated by reference.

EXAMPLES

The following examples are intended to be illustrative, but in no way limiting of the present invention. These examples are not intended to limit the invention or its protection in any way.

Example 1 (pH Sensing)

A 200.0 nanometer silica-based particle comprising a reference dye and a sensor dye based upon the architecture shown in FIG. 1C was synthesized for use as a ratiometric sensor to detect environmental pH.

Synthesis

In an inert gas atmosphere, 3-aminopropyl-triethoxy silane (APTS—Sigma Aldrich Chem. Corp.) was coupled to the isothiocyanate group of the reference dye tetramethylrhodamine (TRITC) at a mole ratio of APTS:TRITC=50:1 in degassed ethanol (Pharmco 200 proof, degassed) to form a TRITC-conjugate. The TRITC conjugate was added under ambient atmosphere to an absolute ethanolic solution of ammonia (2.0M ethanol—Sigma Aldrich Chem. Corp.) and water to which is promptly added the silica precursor tetraethoxysilane (TEOS—99% Sigma Aldrich Chem. Corp.) to yield a final reaction solution of [TRITC-conjugate], [TEOS], [NH$_3$] and [H$_2$O] of $1.7 \times 1^{-5}$ M, 0.17 M, 1.0 M and 2.5 M. This reaction proceeded for 12-18 hrs and a hazy product was collected by centrifugation and resuspended by ultrasonication with water and ethanol.

The particles were resuspended at 0.787 mg/ml in absolute ethanol with appropriate water and NH$_3$ concentrations and a pre-combined solution of TEOS, TRITC-conjugate and ethanol was added drop wise (7.5×10⁻⁷ $M_{TEOS}$/min) to yield a final reaction condition of [TRITC-conjugate], [TEOS], [NH$_3$] and [H$_2$O] of 1.16 mM, 0.27M, 0.2 M and 2.0 M. Following reaction for 12-18 hours, the particles were centrifuged and washed repeatedly with absolute ethanol and deionized water.

A similar synthesis was performed to create a fluorescein (FITC) shell on these particles, using a FITC conjugate synthesized under inert atmosphere at 4.25 mM FITC and a 50:1 molar ratio of APTS to FITC. This conjugate was then added under similar conditions to the TRITC conjugate mixture prepared above with final concentrations of [FITC-conjugate], [TEOS], [NH$_3$] and [H$_2$O] of 0.4 mM, 0.029 mM, 0.2M and 2.0 M for a particle density of 0.787 mg/ml. The particles were approximately 200.0 nanometers in size (FIG. 2C) and comprised a relatively large reference dye rich core and a sensor dye rich shell.

Calibration

Figure 3:
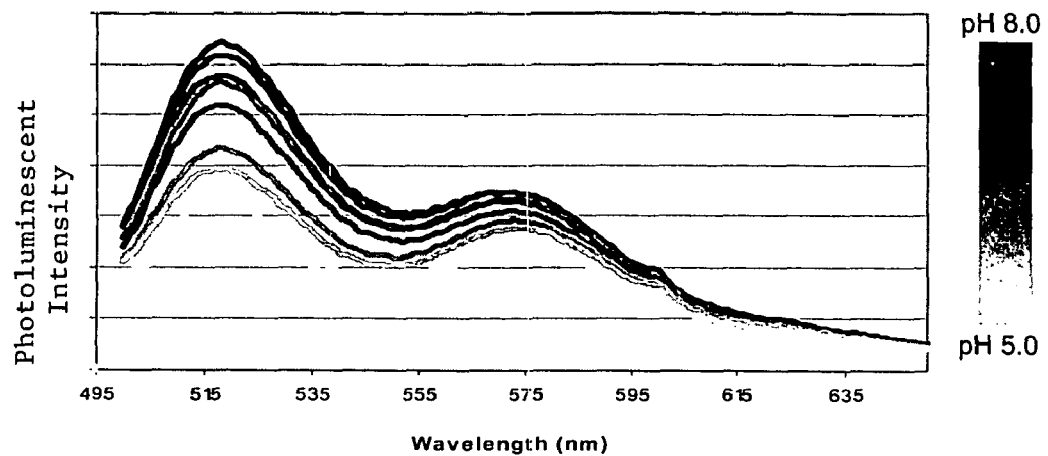
FIG. 3 is a plot of photoluminescent intensity against peak wavelength measurements using the silica-based particles of the present invention in known pH.
Figure 4:
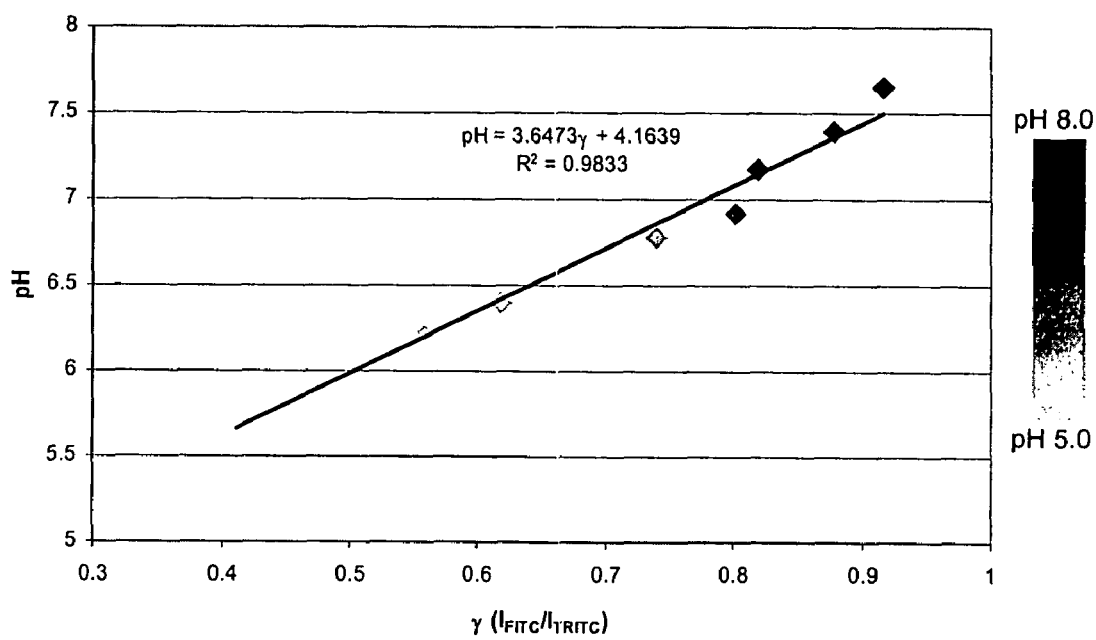
FIG. 4 is a calibration curve depicting the ratios of peak wavelength emissions for the reference and sensor dyes correlated to pH, based on the data collected in FIG. 3.

The particles were diluted from deionized water into sodium phosphate buffers between pH 5 and 9 at 3:20 (v/v) dilutions. The particles were then excited through introduction of a single photon light source at 540.0 nm to excite the tetramethylrhodamine and 490.0 nm to excite the fluorescein. The emission wavelengths were measured by spectrofluorometry (with a Photon Technologies International Spectrofluorometer); maximum peaks are shown in FIG. 3. The larger wavelength peaks correspond to the fluorescein sensor dye while the smaller peaks correspond to the tetramethylrhodamine reference dye. The ratio of peak maxima for emission wavelengths ($\gamma=I_{FITC}/I_{TRITC}$) was then plotted versus pH to give the calibration curves shown in FIG. 4. The calibration curves provide linear calibration over the range of pH from 5-9 for each set of tested particles.

Sensing

The silica-based particles synthesized above may be introduced into a solution of unknown pH. The particles may be excited with the same single photon light source used during calibration at the same excitation wavelengths. The ratio of peak maxima ($\gamma=I_{FITC}/I_{TRITC}$) for emission wavelengths may then be calculated and compared against the calibration curves of FIG. 4. In this way, the pH of the solution may be determined.

Variations, modifications and other implementations of what is described herein will occur to those of ordinary skill in the art without departing from the spirit and scope of the invention. Accordingly, the invention is in no way limited by the preceding illustrative description.

What is claimed is:

1. A silica-based particle comprising a silica-based core and two or more photoluminescent dyes, the two or more photoluminescent dyes comprising at least one reference dye and at least one sensor dye, wherein:
   (a) the reference dye and the sensor dye are chemically different dyes,
   (b) the reference dye and the sensor dye are separated in different compartments of the nanoparticle or are located within the same compartment of the nanoparticle, and
   (c) at least one of the reference dye and the sensor dye is covalently bonded to the silica-based core,
said reference dye exhibiting a relatively constant photon emission and said sensor dye exhibiting different photon emissions in different environments or at different concentrations of an analyte present therein.

2. The silica-based particle of claim 1, wherein the silica-based particle is a nanoparticle.

3. The silica-based particles of claim 1, wherein the silica-based particle comprises pores having diameters ranging from about 0.1 nm to about 100.0 nm.

4. The silica particle of claim 1, wherein one of the reference and sensor dyes comprises between about 1.0 and about 1000.0 dye molecules and the reference and sensor dyes emit photons in response to a single excitation source emitting at a single predetermined wavelength.

5. The silica-based particle of claim 1, wherein the reference dye is positioned within the core and the sensor dye is positioned on at least a portion of a surface of the silica-based particle.

6. The silica-based particle of claim 1, wherein the reference and sensor dyes are positioned on or over the core.

7. The silica-based particle of claim 1, further comprising a silica-based shell surrounding the core, wherein the reference dye is positioned within the core and the silica-based shell is interposed between the reference dye and the sensor dye.

8. The silica-based particle of claim 1, wherein the reference and sensor dyes emit photons in response to a single excitation source emitting at a single predetermined wavelength.

9. The silica-based particle of claim 1, wherein peak wavelengths of the reference and sensor dyes in response to photon exposure are separated by a sufficient gap to individually discern the emission peaks.

10. The silica-based particle of claim 1, wherein exposure of the reference or sensor dye to photon excitation results in infra-red or near infra-red emissions.

11. The silica particle of claim 1, wherein the sensor dye is responsive to at least one of pH, the presence and concentration of ions and chemical or biochemical analytes.

12. The silica-based particle of claim 1, further comprising a surface modifier that exhibits preferential interaction with a target analyte.

13. The silica particle of claim 1, further comprising a therapeutic agent responsive to a disease state or injury.

14. A photoluminescent nanoparticle comprising a porous silica-based core, a silica-based shell surrounding at least a portion of the core and two or more photoluminescent dyes, wherein the two or more photoluminescent dyes comprise at least one reference dye and at least one sensor dye, wherein the reference dye and the sensor dye are chemically different dyes, with the reference dye positioned in the core and the silica-based shell interposed between the reference dye and the sensor dye, said reference dye exhibiting a relatively constant photon emission and said sensor dye exhibiting different photon emissions in different environments or at different concentrations of an analyte present therein.

15. The photoluminescent nanoparticle of claim 14, wherein at least one of the pores includes a diameter between about 0.1 nanometers to about 100.0 nanometers.

16. The photoluminescent nanoparticle of claim 14, wherein a diameter of the nanoparticle is between about 1.0 and 250.0 nanometers.

* * * * *